United States Patent [19]

Sleezer et al.

[11] 4,448,958
[45] May 15, 1984

[54] PURIFICATION OF CEFORANIDE

[75] Inventors: Paul D. Sleezer, Dewitt; Richard R. Smith, Fayetteville, both of N.Y.

[73] Assignee: Bristol-Myers Company, New York, N.Y.

[21] Appl. No.: 435,583

[22] Filed: Oct. 20, 1982

[51] Int. Cl.$^3$ .......................................... C07D 501/20
[52] U.S. Cl. .......................................... 544/20; 544/26
[58] Field of Search ........................................... 544/20

[56] References Cited

U.S. PATENT DOCUMENTS

| | | | |
|---|---|---|---|
| 3,488,730 | 1/1970 | Stephens | 424/246 |
| 3,634,416 | 1/1972 | Schofield | 544/20 |
| 3,634,417 | 1/1972 | Attenburrow | 544/16 |
| 3,766,175 | 10/1973 | Lemieux et al. | 424/246 |
| 3,830,809 | 8/1974 | Brooks, Jr. | 424/246 |
| 3,907,786 | 9/1975 | Naito et al. | 424/246 |
| 3,946,000 | 3/1976 | Naito et al. | 424/246 |
| 3,984,403 | 10/1976 | Fujisawa et al. | 424/246 |
| 4,100,346 | 7/1978 | Gottstein et al. | 544/27 |
| 4,327,279 | 12/1980 | Fisher | 544/16 |

FOREIGN PATENT DOCUMENTS 1265315 3/1972 United Kingdom .
1460327 1/1977 United Kingdom .

OTHER PUBLICATIONS

Leitner et al., Laboratory Evaluation of BL-S786, a Cephalosporin with Broad-Spectrum Antibacterial Activity, Antimicrobial Agents and Chemotherapy, 10(3), 426–435 (Sept. 1976).
Gottstein et al., J. Antibiotics, 29(11), 1226–1229 (1976).
Farmdoc 79940X.
Farmdoc 11639X.
Farmdoc 66666V.
Farmdoc 95117X.
Research Disclosure, 157, 75–76 (May, 1977).

*Primary Examiner*—Paul M. Coughlan, Jr.
*Assistant Examiner*—James H. Turnipseed
*Attorney, Agent, or Firm*—Robert E. Carnahan

[57] ABSTRACT

Crude cephalosporin 7-[α-(2-aminomethylphenyl)acetamido]-3-[(1-carboxymethyltetrazol-5-ylthio)methyl]-3-cephem-4-carboxylic acid is purified by converting it to its salt with benzyldimethylamine, recovering said salt and from it regenerating said cephalosporin in purified form.

6 Claims, No Drawings

PURIFICATION OF CEFORANIDE

BACKGROUND OF THE INVENTION

1. Field of the Invention

This invention relates to antibacterial chemical compounds of the type called cephalosporins and particularly to a chemical method of purifying a particular cephalosporin.

2. Description of the Prior Art

7-[α-(2-Aminomethylphenyl)acetamido]-3-[(1-carboxymethyltetrazol-5-ylthio)methyl]-3-cephem-4-carboxylic acid, for which the U.S. Adopted Name is ceforanide, is also sometimes referred to here and in the literature as BL-S786. For publications on ceforanide see, for example, Leitner et al., Laboratory Evaluation of BL-S786, a Cephalsoporin with Broad-Spectrum Antibacterial Activity, Antimicrobial Agents and chemotherapy, 10(3), 426–435 (Sept. 1976) and Gottstein et al., J. Antibiotics, 29(11), 1226–1229 (1976) and U.S. Pat. No. 4,100,346 (July, 1978). Gottstein et al. used trace amounts of N,N-dimethylbenzylamine as an acid-scavenging agent during preparation of the mixed anhydride of the side chain acid and larger amounts of N-methylmorpholine to dissolve the 3-thiolated-7-aminocephalosporanic acid prior to acylation.

The amines first used with benzylpenicillin have also been disclosed (in general terms and with no information as to solubility) to be capable of forming salts with the acidic carboxyl of cephalosporins including ceforanide (see U.S. Pat. No. 4,100,346). These amines include trialkylamines such as triethylamine, procaine, dibenzylamine, N-benzyl-β-phenethylamine, 1-ephenamine, N,N'-dibenzylethylenediamine, dehydroabietylamine, N,N'-bis-dehydroabietylethylenediamine, and N-(lower)alkylpiperidines such as N-ethylpiperidine; see for example U.S. Pat. Nos. 3,488,730; 3,634,416 (collidine); 3,634,417 (benzylamine); 3,766,175 (which also reviews earlier literature); 3,830,809 (dicyclohexylamine); 3,907,786; 3,946,000 and U.K. Pat. No. 1,265,315 and Farmdoc 79940X (dibenzylamine) and Farmdoc 11639X (N,N'-dibenzylethylenediamine).

For salts or complexes with aminoacids such as lysine, histidine or arginine with other cephalosporins see Farmdoc 66666V and 95117X and U.S. Pat. No. 3,984,403 and U.K. Pat. No. 1,460,327 and with BL-S786 see Research Disclosure, 157, 75–76 (May, 1977).

As used below BDMA means benzyldimethylamine which is also named as N,N-dimethylbenzylamine.

SUMMARY OF THE INVENTION

Methods previously used to purify crude ceforanide produced by acylation of 7-amino-3-(1-carboxymethyl-1H-tetrazol-5-yl)cephalosporanic acid included column chromatography and extensive carbon treatment plus recrystallization at the isoelectric point. This required the use of special columns and acid resistant filters, did not work well with low quality material, produced dilute solutions of the product (as in column eluates) with accompanying losses in mother liquors and did not provide adequate purity, quality (e.g. color) and overall recovery. It is the object of the present invention to overcome these deficiencies.

The objects of the present invention have been achieved by providing the process for the purification of crude ceforanide involving consecutive steps listed below. The process is intended for operation with ceforanide determined by bioassay to be at least 80% pure, but can be modified for purification of material having a purity as low as 62.5% based on bioassay. It is applicable as well to removal of only trace amounts of impurities such as those which cause colored or off-white appearing products. The process steps are as follows:

(a) forming the N,N-dimethylbenzylammonium salt of ceforanide by mixing approximately equimolar amounts of N,N-dimethylbenzylamine (BDMA) and zwitterionic ceforanide using the BDMA in a small molar excess (9–30%), and an aqueous solvent mixture containing a water-miscible substantially neutral organic solvent (preferably in 50% (v/v) aqueous acetone or 50% (v/v) aqueous methanol) and a temperature in the range of 5° C. to 35° C. and preferably 27°–30° C. and pH 7.4–6;

(b) crystallize the salt from solution by adding a further amount of water-miscible neutral organic solvent preferably while warming at 30°–35° C.;

(c) recover the crystalline salt by filtration or centrifugation;

(d) dissolve the crystalline salt in water with adjustment to pH 6.8–7.2 if necessary or in an aqueous water miscible solvent mixture such as aqueous acetone or aqueous methanol which is acidified to less than pH 1.0;

(e) treat the foregoing solution with decolorizing carbon as an optional step to assure production of a pure white product;

(f) remove insolubles and decolorizing carbon by filtration and dilute the filtrate with sufficient of the water miscible organic solvent (acetone or methanol as the case may be) to provide a solvent mixture constituted of 50% by volume of water and 50% by volume of the organic solvent;

(g) adjust to pH 2.3–2.5 using either 6 N aqueous HCl or concentrated aqueous ammonia as the case may be;

(h) allow the product to crystallize at 18°–23° C. for 2 hours with gentle agitation; and (i) recover the crystalline product by filtration or centrifugation.

The intermediate N,N-dimethylbenzylammonium 7-[α-(2-aminomethylphenyl)acetamido]-3-[(1-carboxymethyltetrazol-5-ylthio)methyl]-3-cephem-4-carboxylate provided by this process (step (c)) is a novel substance and is considered part of the present invention.

DESCRIPTION OF SPECIFIC EMBODIMENTS

Example 1

Purification with Acidic Carbon Treatment of BDMA.BL-S786 Salt

In 80 ml. of 1:1 v:v acetone:H$_2$O was slurried 10.0 g. of crude BL-S786, biopotency 743 mcg/mg. The pH was adjusted to 7.7 with 3.25 ml. of N,N-dimethylbenzylamine and a complete solution was obtained. Crystallization was initiated with seed crystals of the BL-S786.amine salt and 160 ml. of acetone added slowly over 30–60 minutes. After stirring 1 hour at room temperature the resulting slurry was cooled to 0°–5° C. and held 2.5 hours. The precipitate was collected by filtration, washed with 60 ml. of 5:1 v:v acetone:H$_2$O followed by 40 ml. of acetone. After drying there was obtained 7.90 g. of BL-S786.BDMA salt.

This solid was added to 150 ml. of H$_2$O plus 75 ml. methanol to give a cloudy solution. The solution was added to 30 g. of p-toluenesulfonic acid.hydrate dissolved in 30 ml. of H$_2$O. To the resulting slightly turbid solution at pH <1.0 was added 1.0 g. of carbon (Darco KB) and the mixture held at about room temperature with stirring 15-20 minutes. The carbon was removed by filtration and washed with 18 ml. H₂O plus 7 ml. MeOH. The resulting clear, nearly colorless solution was adjusted to pH 2.4 with NH₄OH and the product crystallized 1.25 hours at about 25° C. and 1.75 hours at 0°-5° C. The solid was collected by filtration and washed with 70 ml. of H₂O at 0°-5° C. followed by 70 ml. MeOH. After drying there was obtained 5.72 g. of nearly white BL-S786 free acid with excellent ir and nmr spectra and biopotency of 1052 mcg/mg. This represented 81.2% activity recovery.

EXAMPLE 2

Preparation of BDMA.BL-S786 Salt

BL-S876, 1.0 kg., previously determined by bioassay to have a potency of from 800-1000 mcg./mg. but containing colored impurities is dissolved in a mixture of 4.0 l. of water and 4.0 l. of acetone by agitating the pulverized solid with the solvent mixture at a temperature of 26°-30° C. Approximately 0.326 l. of N,N-dimethylbenzylamine (BDMA) is then added and further quantities of BDMA are employed to adjust the pH to pH 7.4-7.6. This is accomplished at 27°-30° C. Complete dissolution of the BL-S786 occurs between pH 6 and pH 7 and crystallization of the BDMA salt commences. If crystallization does not occur, 5 g. of crystalline BDMA.BL-S786 salt from a previous run may be added as seed crystals. After pH 7.4-7.6 has been established, the slurry is warmed to 30°-35° C. and acetone, 16.0 l., which has been prewarmed to that temperature is added during a period of 40-50 minutes with gentle agitation. The batch is then held for 30 minutes at 30°-35° C., and cooled to 0°-5° C. for 2 hours.

The crystalline BDMA.BL-S786 salt is recovered from the foregoing slurry by filtration and is twice washed on the filter with acetone. The cake is dried at 40°-45° C. until the solvent content is less than 2%. The assay is about 825 mcg./mg. by either the bioassay or high performance liquid chromatography methods. The salt is storage stable and may be kept in plastic lined drums in a cold room. The weight yield is a function of the quality of the starting material.

| Assay of Starting Material BL-S786 | Weight Yield of BDMA.BL-S786 Salt |
|---|---|
| 1000 mcg/mg. | 95% |
| 800 mcg/mg. | 85% |

Notes for Example 2

(1) The amine salt may start crystallizing before all of the BL-S786 has dissolved. In this case a complete solution cannot be achieved. The final pH however should be 7.4 to 7.6.

(2) If a very low potency (600-700 mcg/mg.) BL-S786 is being processed, there may be trouble with filtration of the BDMA.BL-S786 salt. This occurs when the added acetone causes precipitation of a gelled material which will tend to slow and possibly stop the filtration. If this occurs the slurry should not be cooled, but should be stirred and filtered at 25°-30° C. Further dilution with 80% acetone/water is sometimes helpful. The amine salt must be washed thoroughly on the filter, or slurried with acetone.H₂O.

(3) The amine salt cake can be processed while it is still damp with acetone. However, the dry weight must be known to proceed properly in the next series of steps given in Example 3 below.

(4) The amine salt produced is nearly pure regardless of the potency (635 mcg/mg. to 923 mcg/mg.) of the crude BL-S786 starting material. Nearly all of the impurities, colored and otherwise, are removed during the filtration and washing of the amine salt cake.

(5) Analytical data for BDMA.BL-S786 salt prepared as described in Example 2 was as follows:

(a) Elemental analysis: Found: C, 52.87; H, 5.08; N, 16.58. Calc'd for $C_{29}H_{34}N_8O_6S_2$: C, 53.16; H, 5.24; N, 17.12.

(b) Infrared, KBr pellet.

| Observed Absorption (cm⁻¹) | Interpretation, Functional Group |
|---|---|
| 3400 | NH and/or OH |
| 3220 } 3020 | $NH_3^\oplus$, $NH^\oplus$ |
| 1770 | β-lactam carbonyl amide carbonyl |
| 1600-1650 | $CO_2^\ominus$ $NH_3^\oplus$ aromatic C=C |
| 1375 | $CO_2^\ominus$ |

(c) Nuclear magnetic resonance (60 MHz)

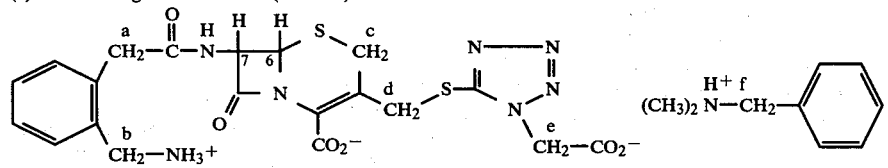

NMR #46211, D₂O Solution

| Chemical Shift (ppm) | Multiplicity | No. of Protons | Functional Group |
|---|---|---|---|
| 7.55 | S | 5 | 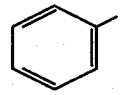 |

| | | | |
|---|---|---|---|
| -continued | | | |
| 7.46 | S | 4 |  |
| 5.6 | D | 1 | $C_7H$ |
| 5.0 | S | 2 | $C_eH_2$ |
| 4.95 | D | 1 | $C_6H$ |
| 4.0–4.5 | M | 6 | $\{ C_fH_2, C_bH_2, C_dH_2 \}$ |
| 3.87 | S | 2 | $C_aH_2$ |
| 3.4–3.7 | M | 2 | $C_cH_2$ |
| 2.88 | S | 6 | $(CH_3)_2N$ |

| NMR #46432 - DMSO/DCl/$D_2O$ Solution | | | |
|---|---|---|---|
| Chemical Shift (ppm) | Multiplicity | No. of Protons | Functional Group |
| 7.3–7.7 | M | 9 |  |
| 5.65 | D | 1 | $C_7H$ |
| 5.3 | S | 2 | $C_eH_2$ |
| 5.05 | D | 1 | $C_6H$ |
| 4.0–4.5 | M | 6 | $\{ C_fH_2, C_bH_2, C_dH_2 \}$ |
| 3.5–4.0 | M | 4 | $\{ C_aH_2, C_cH_2 \}$ |
| 2.75 | S | 6 | $(CH_3)_2N$ |

EXAMPLE 3

Purification with Neutral Carbon Treatment of BDMA.BL-S786 Salt

BDMA.BL-S786 salt prepared as described in Example 2, 1.0 kg., as a lump free crystalline solid is added to 20.1 of tap water at 18°–23° C. Agitation at 18°–23° C. is continued until dissolution is complete (adjust to pH 6.8–7.2, if necessary, using 10% aqueous sodium hydroxide). Decolorizing carbon, 150 g., is then added and agitation at 18°–23° C. is continued for 15 minutes. A diatomaceous earth filter aid, 150 g., is added and the mixture is filtered into a suitable vessel for crystallization of the product. The filter cake is washed with 4.0 l. of water and discarded. The combined filtrate and wash is then diluted with 24 l. of methanol with gentle agitation at 18°–23° C. and the pH of the mixture is adjusted to pH 2.3–2.5 with 6 N HCl. Crystallization is allowed to proceed at 18°–23° C. for 2 hours with gentle agitation. The product is then collected by filtration and washed first with 10.0 l. of water and then with 10.0 l. of methanol. The cake is dried at 40°–45° C. until the volatiles are less than 3% by weight. The dried product is milled to pass a 30 or 40 mesh screen. The weight yield is 752 g. of BL-S786 as a white crystalline solid. The activity yield is 95% from the amine salt and 80–90% over-all. The product may be recrystallized with 96–97% recovery.

The presence of BDMA or of p-toluenesulfonic acid (Example 1) in the product may be determined by thin layer chromatography (TLC). The TLC system used is 10 acetone, 3 benzene, 2 acetic acid, 3 water in parts by volume. In this syste BL-S786 has an Rf of ~0.28, BDMA an Rf of ~0.53 and p-TSA an Rf of ~0.67. All the TLC samples were in solution at alkaline pH. BDMA is diluted with acetone. The other materials were dissolved in phosphate buffer at pH 7.2.

We claim:

1. The process for the purification of ceforanide having from trace amounts up to 36.5% by weight of impurities comprising the consecutive steps of
    (a) forming the salt N,N-dimethylbenzylamine 7-[α-(2-aminomethylphenyl)acetamido]-3-[(1-carboxymethyltetrazol-5-ylthio)methyl]-3-cephem-4-carboxylate by mixing approximately equimolar amounts of N,N-dimethylbenzylamine and zwitterionic 7-[α-(2-aminomethylphenyl)-acetamido]-3-](1-carboxymethyltetrazol-5-ylthio)methyl]-3-cephem-4-carboxylic acid in an aqueous solvent mixture containing a water-miscible neutral organic solvent at a temperature in the range of 5° C. to 35° C.;
    (b) adding a supplementary water-miscible neutral organic solvent to said mixture in sufficient amount of cause precipitation of said salt in crystalline form;
    (c) recoveryng said solid salt;
    (d) dissolving said salt in water or a mixture thereof with a water-miscible organic solvent at substantially neutral or acidic pH; and
    (e) adjusting the solution to pH 2.3–2.5 to precipitate the purified, crystalline, zwitterionic 7-[α-(2-aminomethylphenyl)acetamido)-3-[(1-carboxymethyltetrazol-5-ylthio)methyl]-3-cephem-4-carboxylic acid.

2. The process of claim 1 wherein the ceforanide employed in step (a) has a purity of at least 80%.

3. The process of claim 1 wherein the solution of said salt formed in step (d) is treated with decolorizing carbon.

4. The process of claim 1 wherein said salt in step (d) is dissolved at substantially neutral pH.

5. The process of claim 1 wherein said aqueous solvent mixture in step (a) is a mixture of water and acetone or methanol.

6. N,N-Dimethylbenzylammonium-7-[α-(2-aminomethylphenyl)acetamido)-3-[(1-carboxymethyltetrazol-5-ylthio)methyl]-3-cephem-4-carboxylate.

* * * * *

UNITED STATES PATENT AND TRADEMARK OFFICE
CERTIFICATE OF CORRECTION

PATENT NO. : 4,448,958
DATED : May 15, 1984
INVENTOR(S) : Paul D. Sleezer and Richard R. Smith It is certified that error appears in the above—identified patent and that said Letters Patent is hereby corrected as shown below:

In column 6, line 46, delete the word "of", first occurrence and in its place insert --- to ---

Signed and Sealed this

Twenty-first Day of August 1984

[SEAL]

Attest:

GERALD J. MOSSINGHOFF

Attesting Officer  Commissioner of Patents and Trademarks